(12) United States Patent
Daniele et al.

(10) Patent No.: US 9,720,318 B2
(45) Date of Patent: Aug. 1, 2017

(54) PATTERN DEFINITION OF NANOCELLULOSE SHEETS THROUGH SELECTIVE ASHING VIA LITHOGRAPHIC MASKING

(71) Applicant: The United States of America, as represented by the Secretary of the Navy, Washington, DC (US)

(72) Inventors: Michael A. Daniele, Raleigh, NC (US); Jonathan D. Yuen, Washington, DC (US)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 15/361,171

(22) Filed: Nov. 25, 2016

(65) Prior Publication Data

US 2017/0153541 A1 Jun. 1, 2017

Related U.S. Application Data

(60) Provisional application No. 62/260,415, filed on Nov. 27, 2015.

(51) Int. Cl.
| | |
|---|---|
| *B44C 1/22* | (2006.01) |
| *C03C 15/00* | (2006.01) |
| *C03C 25/68* | (2006.01) |
| *C23F 1/00* | (2006.01) |
| *G03F 7/00* | (2006.01) |
| *C08B 1/00* | (2006.01) |
| *C12P 19/04* | (2006.01) |
| *A61B 5/00* | (2006.01) |

(52) U.S. Cl.
CPC .......... *G03F 7/0002* (2013.01); *A61B 5/6801* (2013.01); *C08B 1/00* (2013.01); *C12P 19/04* (2013.01)

(58) Field of Classification Search
USPC .......................................................... 216/47
See application file for complete search history.

(56) References Cited

U.S. PATENT DOCUMENTS

| | | | |
|---|---|---|---|
| 5,559,057 | A | 9/1996 | Goldstein |
| 7,655,272 | B1 | 2/2010 | Javey et al. |
| 2004/0245209 | A1 | 12/2004 | Jung et al. |
| 2007/0281249 | A1 | 12/2007 | Tutt et al. |
| 2011/0193202 | A1 | 8/2011 | Yu et al. |
| 2015/0072581 | A1* | 3/2015 | Raghu ................... B65D 65/42 442/80 |

OTHER PUBLICATIONS

Ross et al., "Cellulose biosynthesis and function in bacteria." Microbiol Rev. Mar. 1991; 55(1): 35-58.
Castro, C., et al. Bacterial cellulose produced by a new acid-resistant strain of *Gluconacetobacter* genus. Carbohydrate Polymers (2012).
Written opinion of the International Searching Authority in PCT/US2016/063754 dated Mar. 9, 2017.

\* cited by examiner

*Primary Examiner* — Roberts Culbert
(74) *Attorney, Agent, or Firm* — US Naval Research Laboratory; Roy Roberts

(57) ABSTRACT

A masked etching process can prepare patterned nanocellulose for use in conformal electronics such as electrodermal structures might be adhered to human skin.

10 Claims, 6 Drawing Sheets

PATTERN DEFINITION OF NANOCELLULOSE SHEETS THROUGH SELECTIVE ASHING VIA LITHOGRAPHIC MASKING

CROSS-REFERENCE TO RELATED APPLICATIONS

This application is related to the commonly-owned U.S. patent application published as US 2016/0198984 on Jul. 14, 2016, the entirety of which is incorporated herein by reference for the purpose of disclosing and describing the particular materials and methodologies described therein.

BACKGROUND

Wearable devices, such as wear-and-forget health monitoring systems, should ideally be imperceptible. To this end, they preferably conformal to the contours of the skin, self-adhering, ultra-lightweight, and translucent. Existing synthetic ultra-thin polymers possess some of these traits, but in turn present issues of breathability and biocompatibility. The lack of water permeability in these materials prevents chemical contact between the electronics on the substrate and the underlying epidermal layer. Thus, synthetic polymers have limited utility for health applications and struggle to pass biocompatibility protocols.

In a biomaterials context, bio-derived materials, such as silk or fibroin, can be processed in solution form and have potential in niche biomedical applications. These materials, however, rapidly degrade, have poor gas barrier properties, are costly to manufacture, and currently can only form thick sheets due to poor mechanical stability.

For health-related conformal electronics, patterned substrates attuned to specific parts of the body are required. The formation of patterned, freestanding structures in thin films using masked dry etching techniques has been established in synthetic organic films, such as resins (e.g., photoresists), epoxies (e.g., SU-8), polymers (e.g., polyamide) and small molecules (e.g., perylene). These techniques have been mainly limited to microelectromechanical systems (MEMS) and membrane fabrication. Moreover, such freestanding structures are not isolated, as they typically are anchored to a substrate, require an additional backing layer, or are clamped into enclosed spaces.

A need exists for techniques to pattern nanocellulose structures.

BRIEF SUMMARY

Very thin sheets of cellulose, with thicknesses of about a few microns, are naturally conformal, self-adhering, ultra-lightweight, and translucent. Therefore, they are appropriate for applications in which devices have to be imperceptible, such as in wear-and-forget health monitoring systems. Methods described herein were used to form flat, essentially two dimensional nanocellulose structures with micron resolution. Such techniques can be applied to bacterially-grown ultra-thin nanocellulose sheets. The ultra-thinness of the sheets, typically 20 microns and less allows for etching to be performed on them.

More particularly, a pattern is lithographically defined on top of the nanocellulose sheets, which forms a protective layer (lithographic mask) from the etching plasma. Areas not covered by the protective layer are exposed to the plasma and react to form gaseous compounds which decouple from the sheet. A resulting patterned layer of nanocellulose is formed after the etching is complete and the lithographic mask removed.

In one embodiment, a method of patterning nanocellulose includes laminating a sheet of nanocellulose onto a backing substrate, applying a conformal resist coating to the nanocellulose to create a first mask patterned layer having blank areas where the nanocellulose is not covered by the conformal resist coating, thus creating a pre-etch structure comprising the first mask patterned layer atop the sheet of nanocellulose, in turn atop the backing substrate, and then etching to remove portions of the nanocellulose in a pattern corresponding to an inverse of the first mask pattern, thereby creating patterned nanocellulose.

In another embodiment, method of patterning nanocellulose includes laminating a sheet of nanocellulose onto a backing substrate, applying a conformal resist coating to the nanocellulose to create a first mask patterned layer having blank areas where the nanocellulose is not covered by the conformal resist coating, depositing a layer of inorganic material in the blank areas to create a pre-etch structure comprising a pattern of the inorganic material atop the sheet of nanocellulose, in turn atop the backing substrate, removing the first mask pattern layer from the pre-etch structure, and then etching to remove portions of the nanocellulose in a pattern corresponding to the first mask pattern, thereby creating patterned nanocellulose.

BRIEF DESCRIPTION OF THE DRAWINGS

FIG. 9A shows the partially detached kirigami film floating in the water forming a 3D structure, while

DETAILED DESCRIPTION

Definitions

Figure 1:
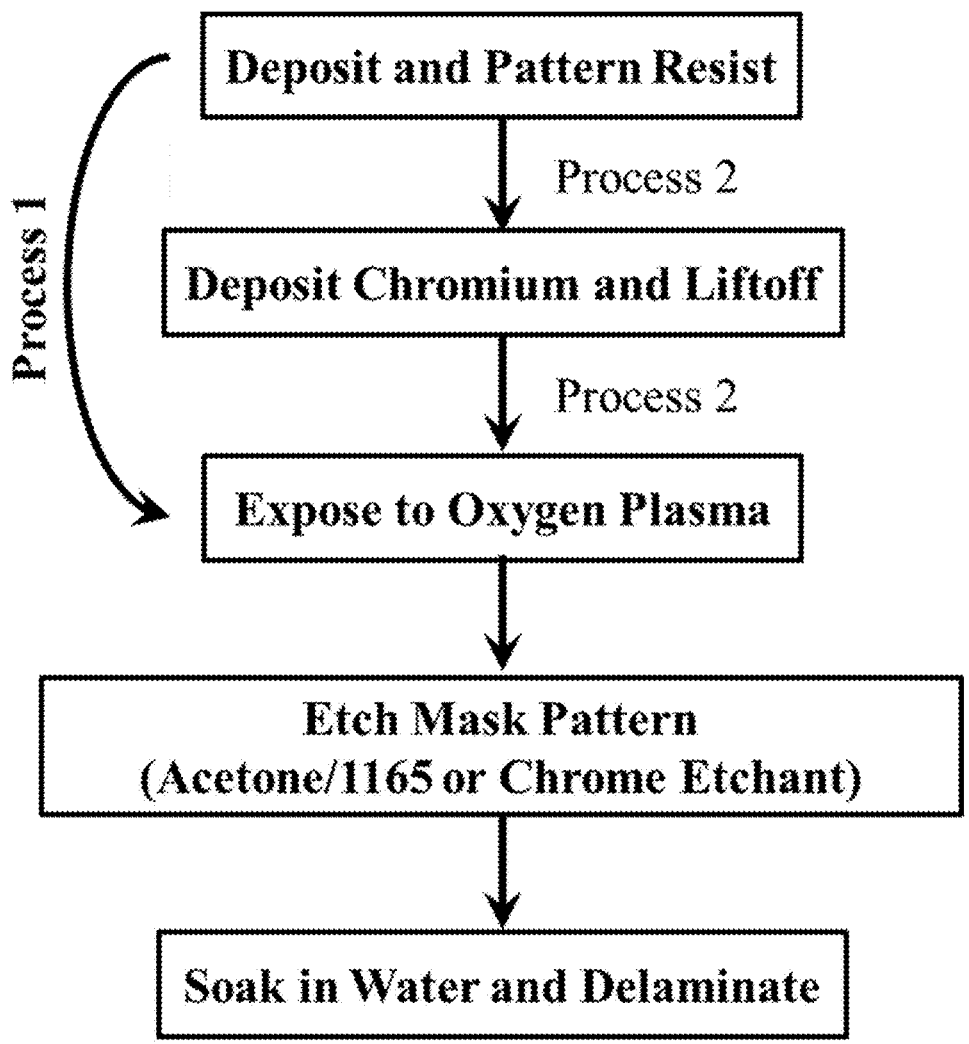
FIG. 1 is a flowchart describing two process flows of fabricating patterned, free-standing nanocellulose sheets.

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used in this specification and the appended claims, the singular forms "a", "an," and "the" do not preclude plural referents, unless the content clearly dictates otherwise.

As used herein, the term "and/or" includes any and all combinations of one or more of the associated listed items.

As used herein, the term "about" when used in conjunction with a stated numerical value or range denotes somewhat more or somewhat less than the stated value or range, to within a range of ±10% of that stated.

As used herein, "nanocellulose" refers to a crystalline or semi-crystalline phase of cellulose in which one dimension is less than 100 nanometers and "microbial nanocellulose" refers to nanocellulose which is generated by the action of living bacteria, for example, *Acetobacter xylinum.*

Overview

Microbial nanocellulose is highly chemical and solvent resistant, mechanically strong, water permeable, and biocompatible. In commercial applications, it appears in the foodstuff "nata de coco." While potential medical applications exist for microbial nanocellulose, currently sheets of such nanocellulose are formed as composites from homogenized suspensions. The problem is that such sheets tend to be too thick and become fragile when wet.

Described herein is a process whereby free-standing patterns of ultrathin nanocellulose, a novel biomaterial class, can be dry plasma-etched from nanocellulose sheets using a lithographically defined mask. This method was used to create two dimensional nanocellulose structures having micron resolution. This invention has pertinence to development of bacterially-grown ultra-thin nanocellulose sheets, which are particularly suited to such etching when they have thicknesses of 20 microns and less, is the reason why etching can be performed on them. Such sheets are particularly suited for use in flexible electronics.

In embodiments, a pattern is lithographically defined on top of the nanocellulose sheets, forming a protective layer (lithographic mask) from the etching plasma. Areas not covered by the protective layer are exposed to the plasma and react to form gaseous compounds which decouple from the sheet. A resulting patterned layer of nanocellulose is formed after the etching is complete and the lithographic mask removed.

Microbial Cellulose

Thin sheets of microbial nanocellulose can be grown in-situ from microbial broth. The nanocellulose is taken out as millimeter-thick layers of gel, which can be laminated on a variety of substrates. The layers can be of any arbitrary size or shape, as determined by dimensions of the growth vat. Upon drying, the layers shrink laterally into sheets with thickness on the order of one or a few microns. These sheets can be easily delaminated from the substrate simply by moistening the sheet, resulting in a freestanding sheet. Moistening the sheet does not return it to the gel state; rather, the sheet-like characteristics are maintained.

For preparing microbial cellulose, *Gluconacetobacter xylinus* is grown in static cultures at 30° C. Sterile Hestrin—Schramm (HS) medium is typically inoculated from a static culture grown in a 50 ml conical tube. Bacterial cells are not easily removed from the pellicle itself and only minimal success has been achieved with using the culture medium either above or below the pellicle. Using this strategy inoculation is more consistent with all cultures forming an initial pellicle between 7-10 days. A second "feed" occurs once the initial basal pellicle has formed. Sterile HS medium is added directly to the surface of the initial pellicle. The culture is then incubated for another 7-10 days during which a second pellicle forms at the air-medium interface. It has been observed that using the "two feed" method forms a more consistent and uniform pellicle than other methods that have been explored to date. Once the upper pellicle has formed to the desire level, both pellicles are transferred to a new larger dish where they are rigorously washed with water to remove some of the HS medium trapped within the pellicle. The water is replaced with a 0.1M NaOH solution and the pellicles in base are transferred to a 90° C. oven for 30-60 minutes. After the base bath pellicles are again rigorously washed with water. Typically washing is done for a minimum of 16 hours will several exchanges over that period. The resultant pellicles are dried and prepared for device fabrication.

Patterning Microbial Cellulose

The original substrate prior to patterning is flat (two-dimensional) in nature, and in general, the resulting structure can be flat as well. However, certain patterns, such kirigami-type patterns, can result in structures that can be three-dimensional.

Figure 2:
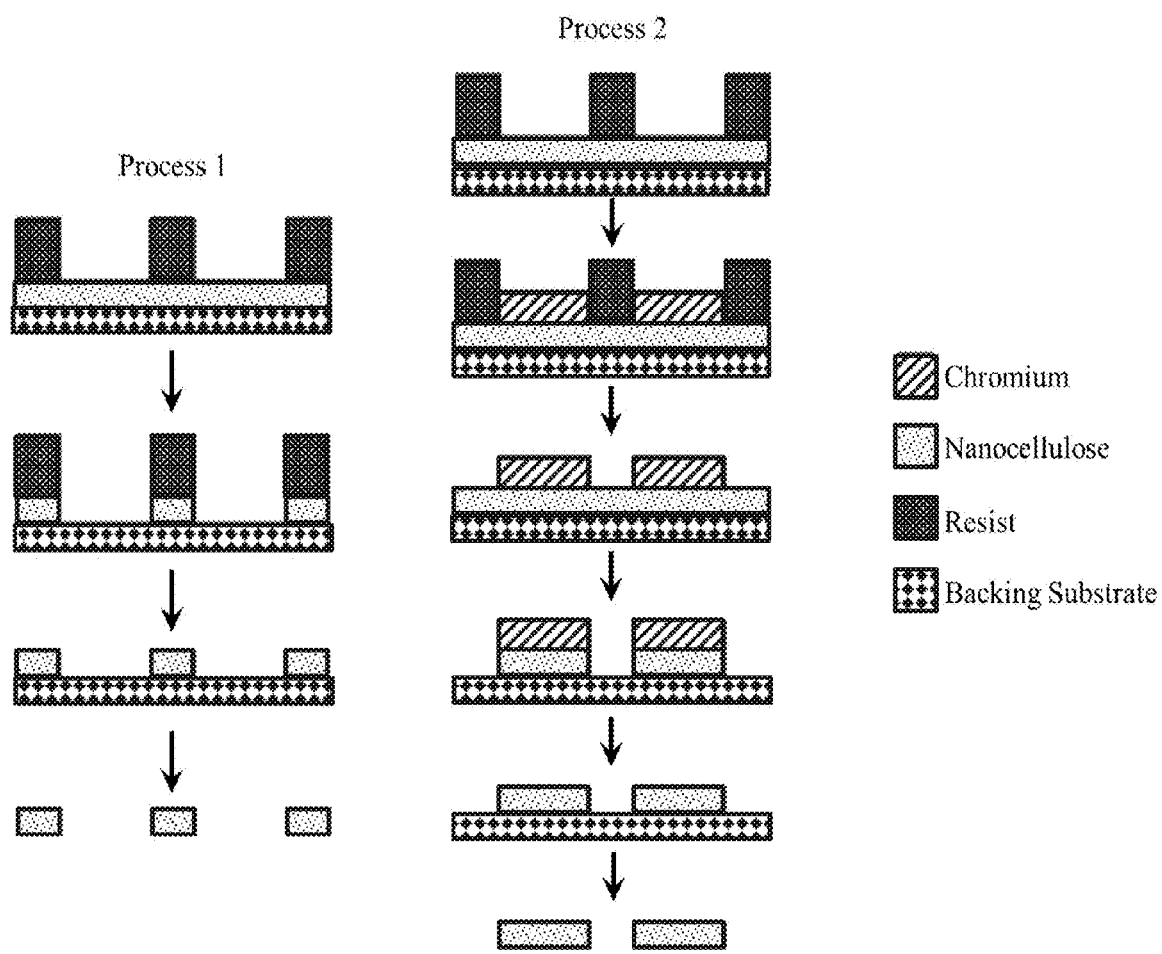
FIG. 2 is a layer-by-layer schematic view of the two process flows as described in FIG. 1. In Process 2, chromium is an exemplary inorganic material.

An exemplary process is described below and corresponds to FIGS. 1 and 2:

1. A layer of nanocellulose gel is laminated onto a rigid substrate which serves as backing during processing.

2. A conformal coating is applied to the surface of the nanocellulose sheet as lithographically patternable layer consisting of resist, or epoxy.

3. The mask pattern is formed, which is either the patterned resist or epoxy layer.

4a. This mask patterned layer acts as the mask for the subsequent plasma etching, OR 4b. The mask patterned layer acts as the immediate layer for the liftoff processing of an inorganic layer, IN WHICH 4c. An inorganic layer, such as metal, is deposited in the areas where the conformal coating (resist) was removed to create a pre-etch structure (the second structure from the top in Process 2 shown in FIG. 2), AND THEN 4d. The remaining resist is removed, resulting in a pattern of inorganic material which is an inverse of the resist pattern. This patterned layer is the mask for the subsequent plasma etching.

5. The entire structure (with organic or inorganic mask) is exposed to a gaseous plasma, which is an electrically excited gas of ions. The gas can either be chemically inert to nanocellulose (e.g. argon) or reactive to nanocellulose (e.g. oxygen). A resist mask will typically be etched in this plasma, and so it either has to be more resistant to etching than the nanocellulose, or it is thicker than the nanocellulose. The metal mask will typically be more resistant to etching (especially in an oxygen plasma).

6. After etching, the mask is removed through wet dissolution, whereby the remaining structure is the patterned nanocellulose.

7. The nanocellulose pattern is immersed in water, whereupon it can be detached from the supporting substrate. Detaching the nanocellulose pattern from the backing substrate requires no complex processing nor harsh chemical environment, as the nanocellulose can merely be moistened and peeled off.

There are many possible sources for nanocellulose that might be patterned: bacterial, tunicate, plant, other biomass, etc.

For the plasma, other gases and gas blends besides oxygen can be used for etching, such as nitrogen, argon, hydrogen, water, xenon difluoride, and halide and halogenated gases. Other techniques for etching can be used, for example wet etching (e.g. Piranha and SC-1), sputter etching, ion beam etching, and descum processes.

Other layers or coatings can be placed on top or below the nanocellulose for etching, which can be exposed to the same etch process as the nanocellulose (in which case, it has to be an organic film), or a different process (for inorganic films).

Devices and/or patterns may have been fabricated onto the nanocellulose or above mentioned layers prior to etching. In this case, the mask layer will also serve to protect the devices and/or structures from the etching process.

Alternative masking methods can be considered, such as batik, lamination, alternative solution coating methods (spray-coating, printing, stenciling), shadow-mask deposition, and selective chemical modification (such as silylation or adduct attachment).

Nanocellulose sheet may optionally carry a thin-film electronic device or series of electronic devices; and the resultant product can be adhered to biological tissue by static forces, conforming to the complex surface terrain of the biological tissue. Electronic devices can include several components, for example conductors, one or more types of sensors (for example, a pressure sensor, pH sensor, strain sensor, and/or a sensor for electrodermal activity), a battery, a transmitter and/or receiver of wireless data, electrodes (optionally configured to transmit electrical energy to the skin), a microprocessor, digital memory, passive and active circuit components, and the like.

Figure 3:
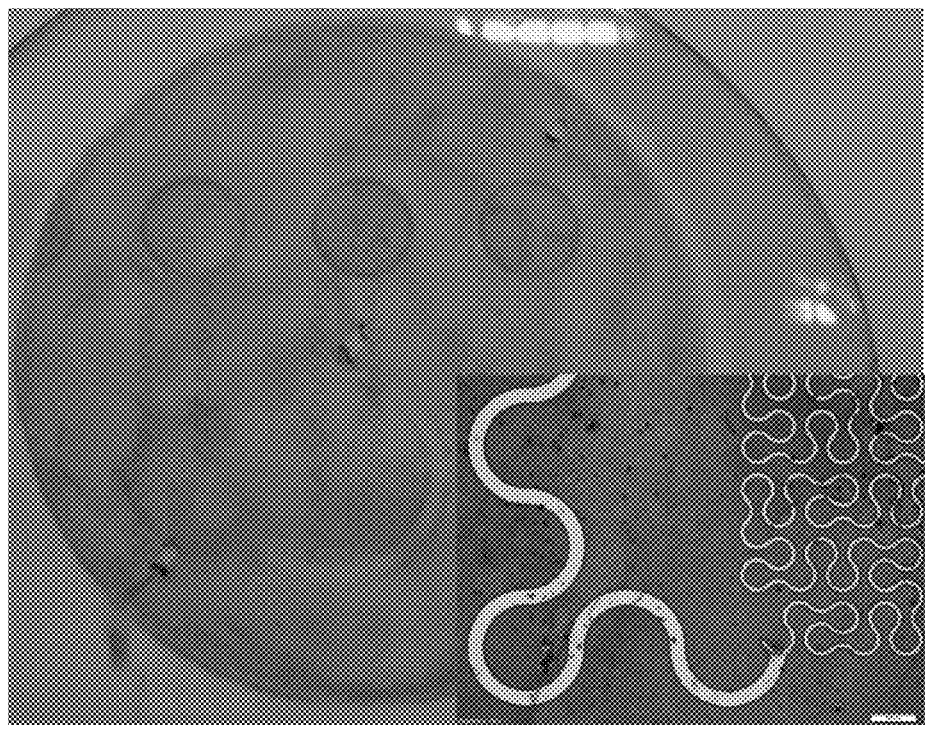
FIG. 3 shows a nanocellulose sheet subjected to the first step of process 1 in FIG. 1—the formation of a resist mask. The outer figure shows a photograph of a Peano curve-based resist mask pattern on the sheet surface. The sheet itself is colored red due to a residual dye from the resist. The inset shows a microscope image of a section of the resist pattern, with part of the Peano curve shown.
Figure 4:
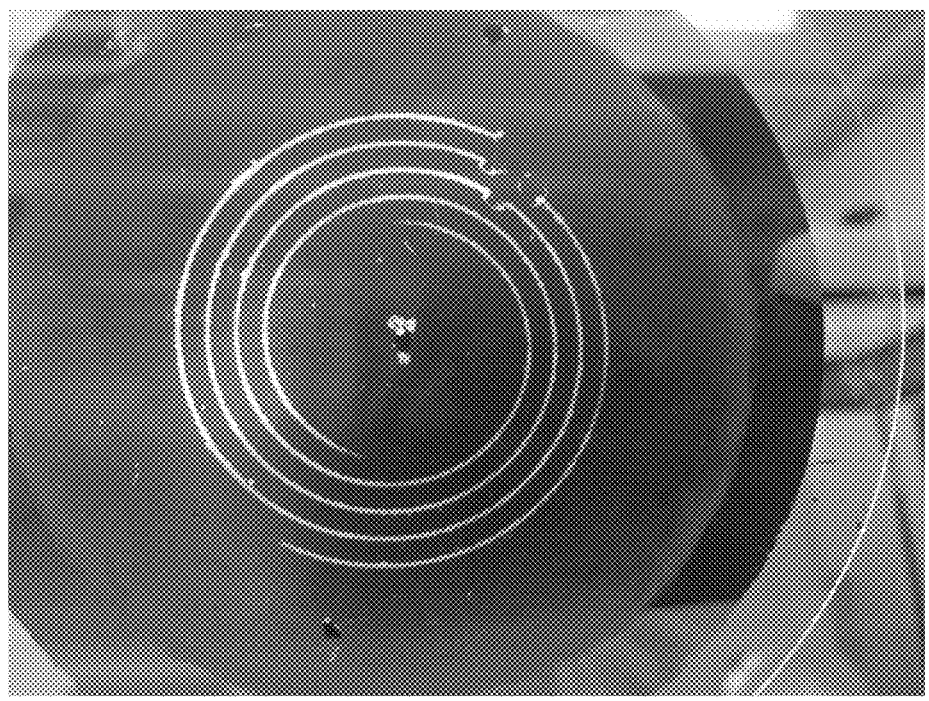
FIG. 4 shows a nanocellulose sheet subjected to the first 3 steps of process 2 in FIG. 1—the formation of the chrome mask, with a kirigami-based chrome mask pattern on the sheet surface.
Figure 5:
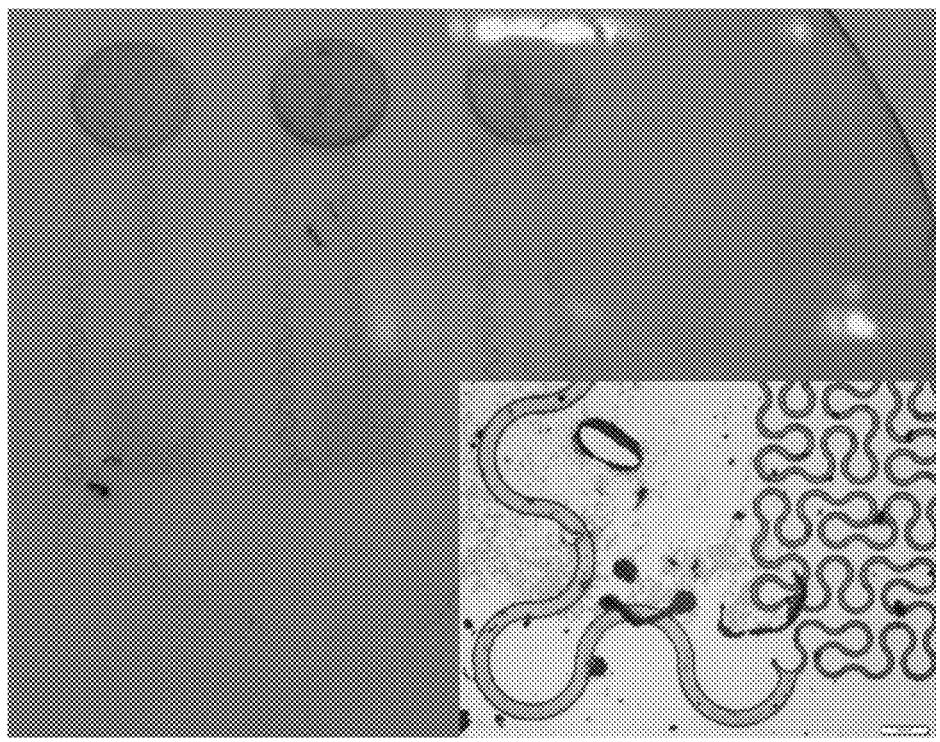
FIG. 5 shows the nanocellulose sample in FIG. 3 after exposure to oxygen plasma. As shown in both the outer photograph and in the inset micrograph, the dusky nanocellulose sheet in the unmasked areas has been removed, revealing the clear, transparent glass substrate underneath.
Figure 6:
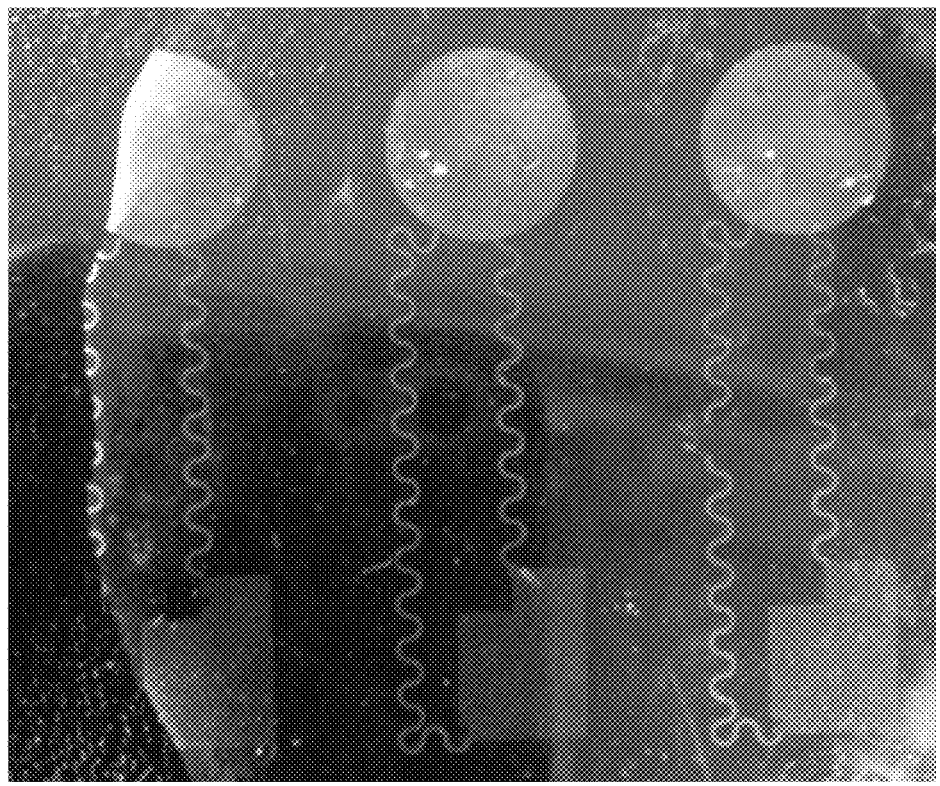
FIG. 6 shows a photograph of the nanocellulose sample in FIGS. 3 and 5 after the resist mask is removed. The red sheet of the resist is gone, with the white, translucent nanocellulose sheet remaining.
Figure 7:
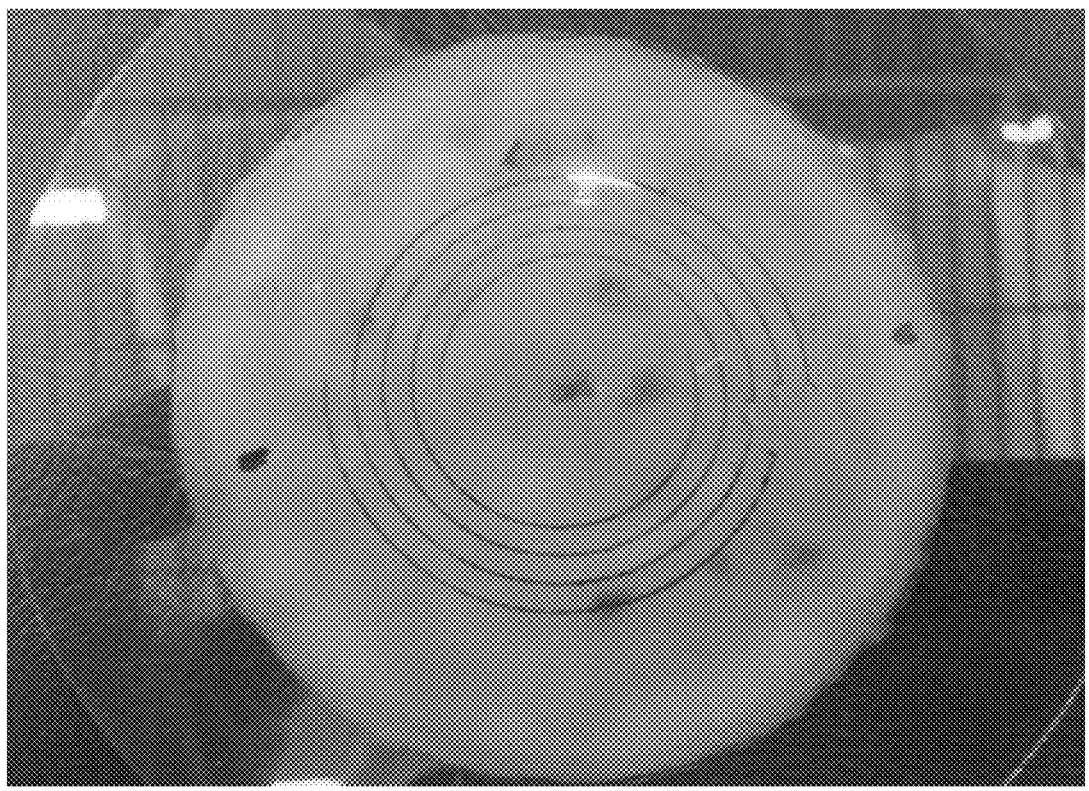
FIG. 7 shows the kirigami-based nanocellulose pattern shown previously in FIG. 4, with the chrome mask removed.
Figure 8:
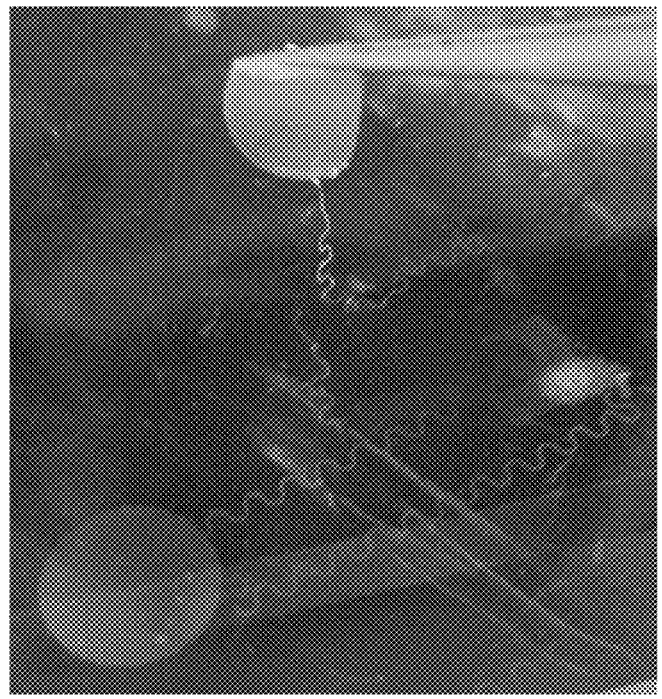
FIG. 8 shows the partial detachment of a Peano curve based nanocellulose pattern after soaking in deionized water, with the pattern partially lifted off from the water surface. Below that is another pattern that has yet to be detached, immersed below the water.
Figure 9A:
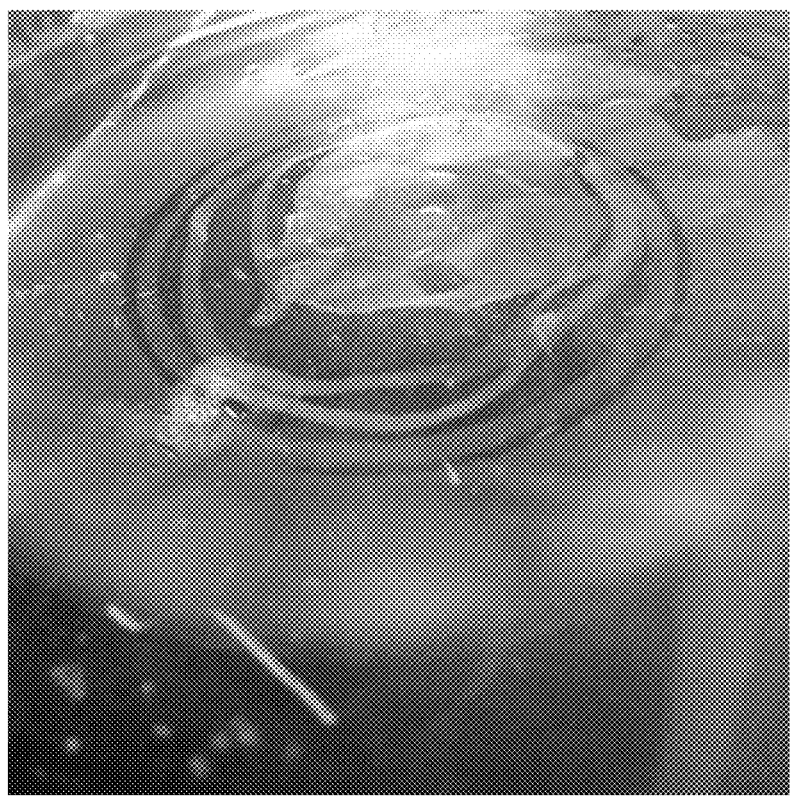
Figure 9B:
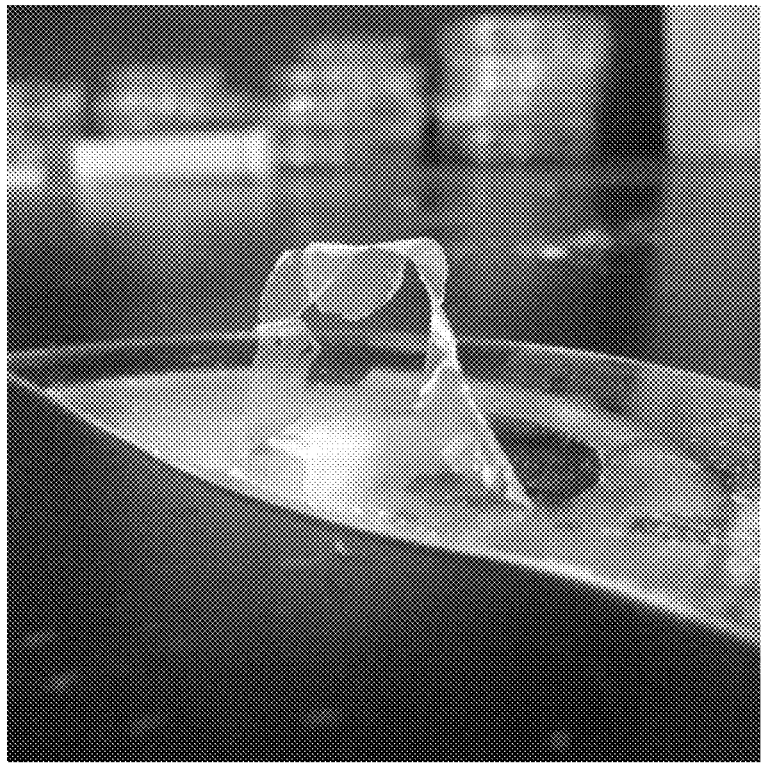
FIG. 9B shows a dried sheet of a different kirigami-based nanocellulose pattern with part of the sheet detached to form a free-standing 3D structure.

Various stages of both processes are shown photographically in the subsequent figures. FIGS. 3 and 4 show finished mask patterns on nanocellulose sheets. FIG. 3 shows a resist-based mask with Peano curves, while FIG. 4 shows a chromium mask with a kirigami-based pattern. In FIG. 3, the nanocellulose sheet is red due to residual dye present in the resist. FIG. 5 shows the resist-masked nanocellulose sheet after exposure to a microwave-powered oxygen plasma etch. In can be seen that, with the exception of the masked areas, the reddish, translucent nanocellulose sheets have been etched away, revealing the clear glass substrate below. On can further observe in FIG. 5 that the dark red resist mask pattern observed in FIG. 3 is reduced to a faint pink film, indicating that the resist has been partially etched away. FIG. 6 shows the Peano curve patterned nanocellulose with the resist removed after soaking in acetone and "1165" (n-methyl pyrrolidinone), while FIG. 7 shows the nanocellulose sheet with kirigami-based pattern after immersion in chrome etchant. One can observe in both sheets that the mask layer has been removed, revealing the translucent, white nanocellulose layer below. FIG. 8 shows the process of detachment of the Peano-curve nanocellulose after soaking in water, with part of one sheet lifted from the water surface. Another sheet remains stuck to the surface of the backing substrate underwater, waiting to be detached. FIG. 9A shows the partially detached sheet of the kirigami structure in water, in which the delaminated section of the sheet has been molded to form a floating 3D structure. FIG. 9B shows a different, more stable kirigami structure forming a freestanding 3D structure.

Concluding Remarks

The technique described herein expands on the capabilities of ultrathin microbial nanocellulose sheets by enabling precise patterns or structures of this material system to be formed at micron resolution. Consisting of interlocking networks of typically micron-long fibers, microbial nanocellulose possesses properties that are optimal for adherence to biological tissue, such as biocompatibility, mechanical and chemical stability, and water and oxygen permeability.

All documents mentioned herein are hereby incorporated by reference for the purpose of disclosing and describing the particular materials and methodologies for which the document was cited.

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

What is claimed is:

1. A method of patterning nanocellulose, comprising:
   laminating a sheet of nanocellulose onto a backing substrate,
   applying a conformal resist coating to the nanocellulose to create a first mask patterned layer having blank areas where the nanocellulose is not covered by the conformal resist coating,
   depositing a layer of inorganic material in the blank areas to create a pre-etch structure comprising a pattern of the inorganic material atop the sheet of nanocellulose, in turn atop the backing substrate,
   removing the first mask pattern layer from the pre-etch structure, and then
   etching to remove portions of the nanocellulose in a pattern corresponding to the first mask pattern, thereby creating patterned nanocellulose.

2. The method of claim 1, further comprising an initial step of growing the nanocellulose in a microbial culture.

3. The method of claim 1, wherein said etching is plasma etching.

4. The method of claim 1, further comprising, after said etching, immersion in water to separate the patterned nanocellulose.

5. The method of claim 1, wherein said sheet of nanocellulose has a thickness of no greater than about 20 microns.

6. A method of patterning nanocellulose, comprising:
   laminating a sheet of nanocellulose onto a backing substrate,
   applying a conformal resist coating to the nanocellulose to create a first mask patterned layer having blank areas where the nanocellulose is not covered by the conformal resist coating, thereby creating a pre-etch structure comprising the first mask patterned layer atop the sheet of nanocellulose, in turn atop the backing substrate, and then etching to remove portions of the nanocellulose in a pattern corresponding to an inverse of the first mask pattern, thereby creating patterned nanocellulose.

7. The method of claim 6, further comprising an initial step of growing the nanocellulose in a microbial culture.

8. The method of claim 6, wherein said etching is plasma etching.

9. The method of claim 6, further comprising, after said etching, immersion in water to separate the patterned nanocellulose.

10. The method of claim 6, wherein said sheet of nanocellulose has a thickness of no greater than about 20 microns.

\* \* \* \* \*